(12) United States Patent
Muni et al.

(10) Patent No.: US 9,095,364 B2
(45) Date of Patent: Aug. 4, 2015

(54) DEVICE AND METHOD FOR DILATING AN AIRWAY STENOSIS

(75) Inventors: Ketan P. Muni, San Jose, CA (US);
Randy S. Chan, San Jose, CA (US);
Sivette Lam, Milpitas, CA (US);
Shrirang V. Ranade, Foster City, CA (US)

(73) Assignee: Acclarent, Inc., Menlo Park, CA (US)

( * ) Notice: Subject to any disclaimer, the term of this patent is extended or adjusted under 35 U.S.C. 154(b) by 0 days.

(21) Appl. No.: 13/551,849

(22) Filed: Jul. 18, 2012

(65) Prior Publication Data

US 2013/0184568 A1    Jul. 18, 2013

Related U.S. Application Data

(60) Provisional application No. 61/512,673, filed on Jul. 28, 2011.

(51) Int. Cl.
| | | |
|---|---|---|
| *A61B 5/05* | (2006.01) | |
| *A61B 17/24* | (2006.01) | |
| *A61M 16/04* | (2006.01) | |
| *A61M 29/02* | (2006.01) | |
| *A61B 6/12* | (2006.01) | |
| *A61M 16/00* | (2006.01) | |
| *A61M 16/08* | (2006.01) | |
| *A61M 25/00* | (2006.01) | |

(52) U.S. Cl.
CPC . *A61B 17/24* (2013.01); *A61B 6/12* (2013.01); *A61M 16/0057* (2013.01); *A61M 16/04* (2013.01); *A61M 16/044* (2013.01); *A61M 16/0488* (2013.01); *A61M 16/0816* (2013.01); *A61M 29/02* (2013.01); *A61M 16/0463* (2013.01); *A61M 25/007* (2013.01); *A61M 25/0026* (2013.01); *A61M 2205/6081* (2013.01)

(58) Field of Classification Search
None
See application file for complete search history.

(56) References Cited

U.S. PATENT DOCUMENTS

| | | | | |
|---|---|---|---|---|
| 4,195,637 A | * | 4/1980 | Gruntzig et al. | 604/509 |
| 4,437,856 A | * | 3/1984 | Valli | 604/29 |
| 4,531,943 A | * | 7/1985 | Van Tassel et al. | 604/523 |
| 4,976,703 A | * | 12/1990 | Franetzki et al. | 604/247 |
| 5,201,723 A | * | 4/1993 | Quinn | 604/264 |
| 5,313,939 A | | 5/1994 | Gonzalez | |
| 5,409,458 A | * | 4/1995 | Khairkhahan et al. | 604/103.08 |
| 5,498,240 A | * | 3/1996 | Bagaoisan et al. | 604/96.01 |

(Continued)

FOREIGN PATENT DOCUMENTS

| | | |
|---|---|---|
| WO | WO 95/01199 A1 | 1/1995 |
| WO | WO 2007/035888 A2 | 3/2007 |

OTHER PUBLICATIONS

International Search Report date Jan. 28, 2013, International Application No. PCT/US2012/047148.

*Primary Examiner* — Nicholas Evoy

(57) ABSTRACT

A medical device and a system and for dilating a stenotic airway of a patient are described. The medical device comprises a proximal end, a distal end, and a shaft system having an inflation lumen and a ventilation lumen the proximal end. The shaft system has a proximal shaft section and a distal shaft section. An inflatable balloon is attached to the distal shaft section in a position that is proximal to the distal end. The ventilating tip is distal to the balloon on the distal shaft section and has one or more radially facing openings. A method for treating a stenotic airway includes inserting the medical device into a patient's airway, and dilating and ventilating the airway.

11 Claims, 2 Drawing Sheets

(56) References Cited

U.S. PATENT DOCUMENTS

| | | | |
|---|---|---|---|
| 5,642,730 A * | 7/1997 | Baran | 128/207.14 |
| 5,715,825 A * | 2/1998 | Crowley | 600/462 |
| 5,718,678 A * | 2/1998 | Fleming, III | 604/43 |
| 5,885,238 A * | 3/1999 | Stevens et al. | 604/6.14 |
| 5,931,730 A * | 8/1999 | Bernhardt et al. | 452/65 |
| 5,964,223 A * | 10/1999 | Baran | 128/207.14 |
| 6,117,106 A * | 9/2000 | Wasicek et al. | 604/96.01 |
| 6,126,634 A * | 10/2000 | Bagaoisan et al. | 604/101.02 |
| 6,146,416 A * | 11/2000 | Andersen et al. | 623/1.15 |
| 6,196,225 B1 | 3/2001 | Allgeyer | |
| 6,217,503 B1 * | 4/2001 | Weinberger et al. | 600/3 |
| 6,293,924 B1 * | 9/2001 | Bagaoisan et al. | 604/103.07 |
| 6,319,248 B1 * | 11/2001 | Nahon | 606/22 |
| 6,500,158 B1 * | 12/2002 | Ikeguchi | 604/319 |
| 6,663,863 B2 * | 12/2003 | Horvath et al. | 424/144.1 |
| RE39,668 E | 5/2007 | Bagaoisan et al. | 604/96.01 |
| 7,410,480 B2 * | 8/2008 | Muni et al. | 604/509 |
| 7,419,497 B2 * | 9/2008 | Muni et al. | 606/196 |
| 7,462,175 B2 * | 12/2008 | Chang et al. | 604/510 |
| 7,469,700 B2 * | 12/2008 | Baran | 128/207.14 |
| 7,472,705 B2 * | 1/2009 | Baran | 128/207.11 |
| 7,520,876 B2 * | 4/2009 | Ressemann et al. | 604/510 |
| 7,641,644 B2 * | 1/2010 | Chang et al. | 604/500 |
| 7,645,272 B2 * | 1/2010 | Chang et al. | 604/509 |
| 7,678,099 B2 * | 3/2010 | Ressemann et al. | 604/510 |
| 7,727,226 B2 * | 6/2010 | Chang et al. | 604/543 |
| 7,785,315 B1 * | 8/2010 | Muni et al. | 604/510 |
| 7,842,062 B2 * | 11/2010 | Keith et al. | 606/199 |
| 7,879,061 B2 * | 2/2011 | Keith et al. | 606/199 |
| 8,012,143 B1 * | 9/2011 | Kampa et al. | 604/532 |
| 8,029,457 B2 * | 10/2011 | Ash et al. | 604/43 |
| 8,080,000 B2 * | 12/2011 | Makower et al. | 604/510 |
| 8,088,101 B2 * | 1/2012 | Chang et al. | 604/96.01 |
| 8,114,062 B2 * | 2/2012 | Muni et al. | 604/509 |
| 8,123,722 B2 * | 2/2012 | Chang et al. | 604/104 |
| 8,267,887 B2 * | 9/2012 | Mohl | 604/102.02 |
| 8,348,969 B2 * | 1/2013 | Keith et al. | 606/199 |
| 8,381,345 B2 * | 2/2013 | Vazales et al. | 15/104.05 |
| 8,388,642 B2 * | 3/2013 | Muni et al. | 606/199 |
| 8,414,473 B2 * | 4/2013 | Jenkins et al. | 600/104 |
| 8,636,724 B2 * | 1/2014 | Wiita et al. | 604/544 |
| 8,920,402 B2 * | 12/2014 | Nash et al. | 604/523 |
| 2001/0010017 A1 * | 7/2001 | Letac et al. | 623/2.11 |
| 2001/0016705 A1 * | 8/2001 | Omaleki et al. | 604/103.06 |
| 2001/0044591 A1 * | 11/2001 | Stevens et al. | 604/6.11 |
| 2002/0010420 A1 * | 1/2002 | Bagaoisan et al. | 604/103.11 |
| 2002/0106369 A1 * | 8/2002 | Horvath et al. | 424/131.1 |
| 2002/0111584 A1 * | 8/2002 | Walker et al. | 604/113 |
| 2003/0009132 A1 * | 1/2003 | Schwartz et al. | 604/152 |
| 2003/0163148 A1 * | 8/2003 | Wang et al. | 606/159 |
| 2003/0229307 A1 * | 12/2003 | Muni et al. | 604/103.02 |
| 2004/0073162 A1 * | 4/2004 | Bleam et al. | 604/103 |
| 2004/0116845 A1 | 6/2004 | Darouiche et al. | |
| 2004/0122456 A1 * | 6/2004 | Saadat et al. | 606/157 |
| 2004/0123869 A1 | 7/2004 | Rutter | |
| 2004/0176837 A1 * | 9/2004 | Atladottir et al. | 623/1.35 |
| 2004/0210187 A1 * | 10/2004 | Zawacki | 604/43 |
| 2004/0267196 A1 * | 12/2004 | Miki et al. | 604/103.04 |
| 2006/0074396 A1 * | 4/2006 | Stiger | 604/509 |
| 2006/0106361 A1 * | 5/2006 | Muni et al. | 604/500 |
| 2007/0208301 A1 * | 9/2007 | Evard et al. | 604/103.1 |
| 2007/0282303 A1 * | 12/2007 | Nash et al. | 604/510 |
| 2008/0033477 A1 * | 2/2008 | Campbell et al. | 606/194 |
| 2008/0082080 A1 * | 4/2008 | Braga | 604/523 |
| 2008/0103521 A1 * | 5/2008 | Makower et al. | 606/196 |
| 2008/0183128 A1 * | 7/2008 | Morriss et al. | 604/35 |
| 2008/0234720 A1 * | 9/2008 | Chang et al. | 606/196 |
| 2008/0275483 A1 * | 11/2008 | Makower et al. | 606/192 |
| 2008/0281156 A1 * | 11/2008 | Makower et al. | 600/118 |
| 2008/0319424 A1 * | 12/2008 | Muni et al. | 604/890.1 |
| 2009/0028923 A1 * | 1/2009 | Muni et al. | 424/434 |
| 2009/0062725 A1 * | 3/2009 | Goebel | 604/28 |
| 2009/0107503 A1 * | 4/2009 | Baran | 128/204.25 |
| 2009/0187098 A1 * | 7/2009 | Makower et al. | 600/424 |
| 2009/0221988 A1 * | 9/2009 | Ressemann et al. | 604/514 |
| 2009/0260625 A1 * | 10/2009 | Wondka | 128/203.12 |
| 2009/0312745 A1 * | 12/2009 | Goldfarb et al. | 604/514 |
| 2010/0076416 A1 * | 3/2010 | Hoey et al. | 606/2 |
| 2010/0121308 A1 * | 5/2010 | Muni et al. | 604/514 |
| 2010/0145187 A1 * | 6/2010 | Weber et al. | 600/424 |
| 2010/0168511 A1 * | 7/2010 | Muni et al. | 600/104 |
| 2010/0174308 A1 * | 7/2010 | Chang et al. | 606/199 |
| 2010/0185156 A1 * | 7/2010 | Kanner et al. | 604/190 |
| 2010/0198137 A1 * | 8/2010 | Broaddus et al. | 604/28 |
| 2010/0198191 A1 * | 8/2010 | Clifford et al. | 604/514 |
| 2010/0198247 A1 * | 8/2010 | Chang et al. | 606/185 |
| 2010/0199448 A1 * | 8/2010 | Vazales et al. | 15/104.05 |
| 2010/0268245 A1 * | 10/2010 | Chang et al. | 606/108 |
| 2010/0274188 A1 * | 10/2010 | Chang et al. | 604/96.01 |
| 2010/0280450 A1 * | 11/2010 | Jain | 604/96.01 |
| 2011/0004057 A1 * | 1/2011 | Goldfarb et al. | 600/106 |
| 2011/0023887 A1 * | 2/2011 | Vazales et al. | 128/207.14 |
| 2011/0023888 A1 * | 2/2011 | Vazales et al. | 128/207.14 |
| 2011/0034828 A1 * | 2/2011 | Holmin et al. | 600/567 |
| 2011/0082483 A1 * | 4/2011 | Diamant et al. | 606/159 |
| 2011/0112512 A1 * | 5/2011 | Muni et al. | 604/514 |
| 2011/0245800 A1 * | 10/2011 | Kassab et al. | 604/506 |
| 2011/0288477 A1 * | 11/2011 | Ressemann et al. | 604/95.04 |
| 2012/0071824 A1 * | 3/2012 | Chang et al. | 604/96.01 |
| 2012/0130391 A1 * | 5/2012 | Sundt et al. | 606/108 |
| 2012/0150119 A1 * | 6/2012 | Schaeffer et al. | 604/164.06 |
| 2012/0172912 A1 * | 7/2012 | Ressemann et al. | 606/196 |
| 2012/0192872 A1 * | 8/2012 | Rudakov et al. | 128/831 |
| 2013/0019864 A1 * | 1/2013 | Wondka | 128/200.26 |

\* cited by examiner

DEVICE AND METHOD FOR DILATING AN AIRWAY STENOSIS

FIELD OF THE INVENTION

The present invention relates, in general, to medical devices and, in particular, to medical devices and related methods for treating a stenosis in an airway of a patient.

BACKGROUND OF THE INVENTION

Airway stenosis (or "airway narrowing") is a medical condition that occurs when some portion of a patient's airway becomes narrowed or constricted, thus making breathing difficult. A stenosis may occur in any part of the airway, i.e. larynx, trachea, bronchi or a combination (laryngotracheal or tracheobroncial stenosis) in adults or children and due to any of several different causes. By far the most common airway stenoses (approximately 95%) are acquired, meaning the patient is not born with the condition, and the most common cause of airway stenosis is trauma caused by intubation (a tube placed in the airway for ventilation/breathing assistance in a patient who cannot breathe). Intubation for prolonged periods of time may traumatize the airway, causing scar tissue formation that forms the stenosis. Sometimes the cause of stenosis is unknown, such as in idiopathic subglottic stenosis. Managing airway stenosis is one of the most challenging problems for an ENT (ear, nose and throat) surgeon.

Subglottic stenosis is one form of airway stenosis that occurs in the larynx, below the glottis (the area of the larynx around the vocal chords). The disorder can either be congenital or acquired and can affect both adults and children. Acquired subglottic stenosis is the most commonly acquired anomaly of the larynx in children and the most common abnormality requiring tracheotomy in children younger than one year. To correct subglottic stenosis, the lumen of the cricoids area is expanded to increase airflow during breathing. Surgical correction of subglottic correction of subglottic stenosis has been performed with various techniques over the years.

Therapies for treating airway stenosis range from endoscopic treatments, such as dilation and laser resection, to open procedures such as laryngotracheal reconstruction. In one technique, a series of rigid dilators of increasing diameter are pushed down the airway, gradually expanding the constriction but also applying unwanted shear forces to the airway. More recently, balloon catheters have been used to perform airway dilation. Such a balloon procedure is described, for example, in US Patent Publication No. 2010/0168511 which is incorporated herein by reference in its entirety. The system described in that patent application is configured for use in an airway and describes a system for dilating a stenotic region with a catheter shaft having an overall length of less than 70 cm, an inflatable balloon disposed along a distal portion of the catheter shaft, and a stylet. The method for dilating a stenotic region in an airway includes advancing a balloon catheter through the airway of a patient to position an inflatable balloon of the catheter within at least a portion of the stenotic region, maintaining a position of the catheter relative to the patient and inflating the balloon to dilate the stenotic region.

Methods and devices for improved patient comfort would allow for patient ventilation during dilation of the stenotic region in the airway and increased flexibility for the physician with regard to duration of dilation and number of inflation and deflation cycles. These objectives are addressed by the embodiments described in this application.

SUMMARY OF THE INVENTION

Accordingly, in one aspect the invention is directed to medical device for dilating an airway stenosis. The device comprises a proximal end, a distal end and a shaft system. The shaft system has an inflation lumen and a ventilating lumen between the proximal and distal ends of the device. The shaft system has a proximal shaft section and a distal shaft section with an inflatable balloon on the distal shaft section, proximal to the distal end of the medical device. The distal shaft section further has a ventilating tip distal to the inflatable balloon, the ventilating tip having a tip opening and one or more radially facing openings.

In one embodiment, the medical device of has four radially facing openings. In another embodiment the radially facing openings have a diameter of between 1 mm and 2 mm and may be spaced 90 degrees apart.

In other embodiments, the inflation and ventilating lumens are adjacent lumens. In still other embodiments the medical device has an atraumatic tip portion, and may incorporate direct visualization markers and/or one or more radiographic markers. In some embodiments, the markers are located on the shaft system and in other embodiments the markers are located on the balloon. In some embodiments, the ventilating tip comprises a soft and atraumatic tip portion, and in other embodiments the soft and atraumatic tip portion is a slanted soft and atraumatic tip portion.

In another aspect, the invention is directed to a connector for connecting a medical device to a ventilation source and an inflation source. The connector has a ventilation port and an inflation port. The ventilation port and the inflation port are either ports of different sizes, ports of different shapes or ports of different connection types. The inflation source is water, saline or contrast agent and the ventilation source is oxygen or air.

In one embodiment of the connector, the inflation port has a threaded connector and the ventilation port has a non-threaded connector or in another embodiment, the inflation port has a non-threaded connector and the ventilation port has a threaded connector. In other embodiments, the inflation port has a right-handed threaded connector and the ventilation port has a left-handed threaded connector or the inflation port has a left-handed threaded connector and the ventilation port has a right-handed threaded connector. In another embodiment of the connector, the ventilation port is larger in diameter than the inflation port In another aspect, the invention is directed to a packaged kit for treating an airway stenosis. The kit contains a medical device having an inflation lumen, a ventilating lumen, an inflatable balloon and a ventilating tip, the inflation lumen and the ventilating lumen being adjacent lumens and the ventilating tip comprising at least one radially facing opening, an optional balloon insertion stylet for insertion of the medical device into the anatomy, and ventilating tubing for connecting the medical device to a ventilation source. In another embodiment, the packaged kit contains a medical device having an inflation lumen, a ventilating lumen, an inflatable balloon and a ventilating tip, the inflation lumen and the ventilating lumen being adjacent lumens and the ventilating tip comprising at least one radially facing opening and a balloon insertion stylet for insertion of the medical device into the anatomy In a further aspect, the invention is directed to a method for treating a stenotic region in the airway of a human patient.

The method comprises providing a medical device having an inflation lumen, a ventilating lumen, an inflatable balloon and a ventilating tip, the inflation lumen and the ventilating lumen being adjacent lumens and the ventilating tip comprising a tip opening and at least one radially facing opening, inserting the medical device into an airway, positioning the medical device in the airway at the stenosis, inflating the balloon to dilate the airway, deflating the balloon, and optionally repeating the inflating and deflating steps and withdrawing the medical device from the airway. The oxygen is delivered through the ventilating lumen before, during or after the inflating step.

In another embodiment, the method comprises providing a medical device having an inflation lumen, a ventilating lumen, an inflatable balloon and a ventilating tip, the inflation lumen and the ventilating lumen being adjacent lumens and the ventilating tip comprising a tip opening and at least one radially facing opening, inserting the medical device into an airway, positioning the medical device in the airway at the stenosis, inflating the balloon to dilate the airway, deflating the balloon, and optionally repeating the inflating and deflating steps and withdrawing the medical device from the airway. Air is inspired through the ventilating lumen before, during or after the inflating step.

In a further embodiment, the stenotic region is in the airway portion selected from the group consisting of larynx, trachea and bronchi.

DETAILED DESCRIPTION

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

Medical devices according to embodiments of the present invention are beneficial in that, for example, their configuration provides for a particularly efficient preparation and treatment of a patient's airway and is mechanically simple. Moreover, the simplicity of the medical devices provides for them to be manufactured in a cost effective manner. In addition, the medical device according to embodiments of the present invention is sufficiently stiff that it can be beneficially employed to access the airway with or without the additional use of a stylet.

Figure 1:
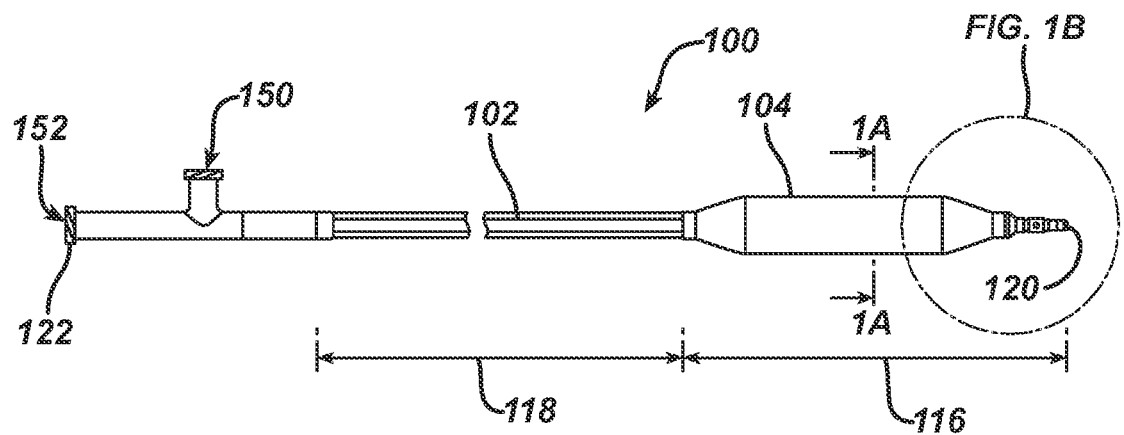
FIG. 1 is a simplified side view of a medical device according to an embodiment of the present invention.
Figure 1A:
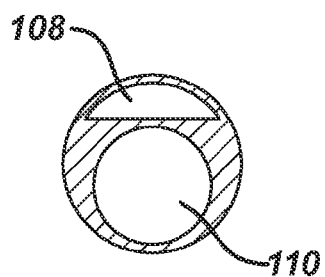
FIG. 1A is a cross section view through line 1A-1A of FIG. 1.
Figure 1B:
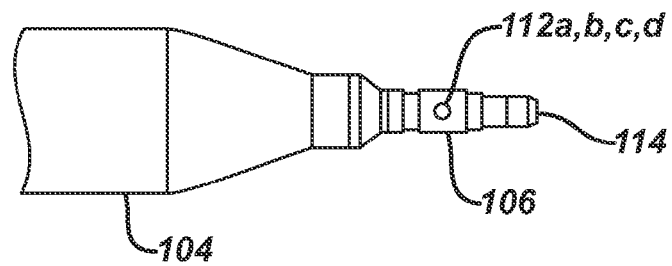
FIG. 1B is an enlarged side view of the distal end of the medical device of FIG. 1.

FIG. 1 is a simplified side view of a medical device 100 for the treatment of an airway stenosis according to an embodiment of the present invention. The medical device 100 is an airway dilation and ventilating catheter with an integrated shaft system 102. The shaft system 102 has a distal shaft portion 116 and a proximal shaft portion 118 and the medical device has a distal end 120 and a proximal end 122. The distal shaft portion 116 is surrounded by a high pressure balloon 104 located near the ventilating tip 106. The shaft system 102 contains adjacent dual lumen tubing (see FIG. 1A). By adjacent dual lumen tubing is intended that the lumens are next to each other and are spaced apart, one from the other. The inflation lumen 108 is used for inflation of the balloon with water, contrast medium or saline through inflation port 150 located near the proximal end 122 of medical device 100, and the ventilating lumen 110 permits passage of oxygen from the ventilation port located near the proximal end 122 of medical device 100 to facilitate ventilation of the patient and prevent negative pressure pulmonary edema due to attempted breathing during the dilation procedure and the resultant airway blockage. The inner diameter of the ventilation lumen is between about 2 mm and about 4 mm, and is often about 4 mm. The ventilation lumen is patent during inflation of the balloon, that is, the shaft may be made of pebax 72D or nylon 12 or similar non-collapsing materials to ensure that the ventilation lumen does not collapse during balloon inflation. In an alternative embodiment, a third lumen may be included as a separate stylet insertion lumen, such that the shaft system comprises an inflation lumen, a ventilating lumen, and a stylet insertion lumen. Alternative designs wherein the inflation lumen and the ventilating lumen are coaxial lumens, or all three lumens are coaxial lumens are also contemplated herein.

The medical device 100 has a ventilating tip 106 with both a forward facing tip opening 114 and radially facing openings 112a, 112b, 112c and 112d to facilitate oxygen flow through the ventilating lumen 110. The medical device 100 is intended to dilate an airway stenosis and to provide a means to ventilate the airway during the dilation procedure. The medical device 100 is designed to ventilate through the tip opening 114 and four radially facing openings 112a, 112b, 112c and 112d in the ventilating tip 106, by delivering oxygen via the ventilating lumen 110 for delivery before, during, or after dilation of the airway stenosis. By radially facing openings is intended that the flow through the openings may be at 90 degrees from the flow through the tip opening, but is may also be at 30, 45 or 60 degrees or other angles between 0 and 90 degrees, and the openings may be round or non-round such as oval or slot-shaped. The ventilating tip 106 is located on the distal shaft section 116, distal to the distal end of the balloon 104.

The balloon 104 is designed to be non-compliant or semi-compliant, but in certain embodiments may also be compliant. The diameter of the non-compliant balloon does not vary significantly with inflation pressure and that of the semi-compliant balloon will vary only to the extent that it will "hourglass" or "dog-bone" about a target region. The balloon itself may be any shape such as round, triangular, oval or square. In the embodiment shown in FIG. 1, the balloon is round and semi-compliant.

In some embodiments, direct visualization markers and/or radiographic markers may be disposed along the integrated shaft system 102. Generally, "direct visualization markers"

refers to markers that may be viewed during use with the naked eye or by use of an endoscope, while "radiographic markers" include radiopaque material and are viewed using a radiographic device such as intra-operative fluoroscopy. Direct visualization markers can be positioned in a number of locations along the integrated shaft system 102, including the segment of the shaft system inside the balloon and may also be incorporated onto the balloon itself. A shaft system 102 may have a dark color, such as black, dark blue, dark grey or the like, and markers may have a light color, such as white, yellow, green, red or the like. In some embodiments, markers may have different colors and/or different widths to facilitate distinguishing the markers from one another during use. This contrast in colors may facilitate viewing the markers in a darkened operation room and/or when using an endoscope inside a patient in the presence of blood. The endoscope may be inserted into the ventilation lumen at any time before, during, or after the procedure to aid in visualization of the airway and of the stenosis and/or to aid in insertion of the medical device. Radiographic markers are often used to ensure proper alignment of the balloon with the stenosis.

The medical device 100 may be packaged with a balloon insertion stylet and ventilation tubing. The insertion stylet assists with insertion of the medical device 100 into the airway and is removed from the device 100 prior to inflation of the balloon. The ventilation tubing incorporates standard connectors on each end and is used to attach a source of oxygen to the ventilation port 152 of the medical device 100 for airway ventilation. The medical device 100 may also be packaged with an insertion stylet alone where the ventilation source is the ambient air.

Airway access is achieved by inserting the medical device 100 into the airway, advancing the medical device and positioning the balloon 104 at the site of the stenosis. The medical device 100 is then inflated to dilate the airway. Following dilation, the balloon is deflated. The process of inflation and deflation may be repeated 2, 3, 4 or more times. An oxygen source is connected to the ventilation port 152 of the medical device 100. Oxygen is delivered to the ventilation lumen through the ventilation tip 106 via the distal tip opening 114 and four radially facing openings 112a, 112b, 112c and 112d of the medical device 100, each side port having a diameter of 0.157 inches (4 mm). Oxygen may be delivered before, during or after inflation of the balloon. Alternatively, the ventilation source may be the ambient air, and the ventilation port 152 may be open to the atmosphere. Upon completion, the medical device 100 is removed from the anatomy. Ventilation of the patient during the procedure allows for prolonged duration of balloon inflation, and the ability to repeat the inflation, deflation procedure multiple times while maintaining oxygen saturation of the patient. While the procedure may be done in the operating suite of a hospital, it may also be done in an out-patient surgery center or a doctor's office.

The medical device 100 may have any number of suitable sizes, shapes and configurations. For example, the balloon 104 may have different lengths and diameters in different embodiments, to accommodate different patient anatomies. The overall catheter length and diameter may also vary. In some embodiments, for example, the overall length of the medical device 100 from the proximal end 122 to the distal end 120 is about 35-70 cm, often less than or equal to about 50 cm, and often about 45 cm.

The working length of the balloon 104 may be about 40 mm. By "working length" it is meant the length between the two tapered portions of the balloon 104 may range from between about 10 mm to about 60 mm and often from about 16 mm to about 45 mm. A variety of lengths may be provided, including about 16 mm, 24 mm and 40 mm. The outer diameter of the fully inflated working length of the balloon 104 may also vary. The balloon may have inflated diameter in the range of about 3 mm to about 24 mm and often about 5 mm to about 20 mm. In one embodiment, a variety of diameters may be provided, including about 5 mm, about 7 mm, about 10 mm, about 14 mm, about 20 mm and about 24 mm. For example, a combination of balloon sizes and lengths may be provided, such that a physician may choose an appropriate size for an adult or pediatric patient. In one example, the following combinations may be provided (first dimension is diameter, second is length): 5 mm×24 mm; 7 mm×24 mm; 8 mm×24 mm, 8.5 mm×24 mm, 8.5 mm×40 mm, 10 mm×40 mm; and 14 mm×40 mm. Of course, any of a number of other combinations of sizes of balloons 104 may be provided.

The balloon 104 is made of any suitable material known in the art for inflation balloons and may be constructed of semi-compliant or non-compliant materials such as nylon (semi-compliant) and polyethylene terepththalate (PET) (non-compliant). The atraumatic tip portion 106 is made of nylon with 20% barium sulfate and is approximately 10 mm in length (it may be between about 5 mm and 20 mm in length) and may contain a radiopaque marker for fluoroscopic visualization in the patient anatomy. The combination of materials (the nylon balloon and the adjacent dual lumen design) provides for ease of insertion of the medical device into and removal from the airway. The soft and atraumatic nature of the tip further prevents injury of the airway during deployment of the medical device 100 and allows for collapse and low profile of the tip during insertion of the medical device 100.

Referring now to FIG. 1, in one embodiment, medical device 100 may include a forward facing tip opening 114 and four radially facing openings 112 a, 112b, 112c and 112d, on irrigation tip 106 spaced 90 degrees apart, with the inner diameter of the forward facing tip opening being 0.157 inches (4 mm) and each of the side openings having a inner diameter of between about 1 and 2 mm and the outer diameter of the integrated shaft system 102 being about 0.236 inches (6 mm). Alternative embodiments may include any suitable alternative number of side openings (1 to 4, 5, 6 or more) distributed in any suitable pattern such as a helical pattern. Each side opening may have any suitable diameter in various alternative embodiments. For example, in one embodiment, each side opening may have a diameter of between about 0.5 mm and about 3 mm and often between about 1 and 2 mm.

Figure 2:
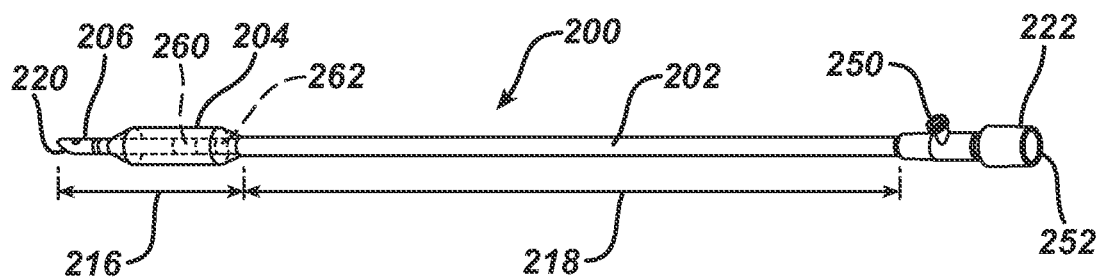
FIG. 2 is a perspective view of a second embodiment of the medical device of the present invention.
Figure 2A:
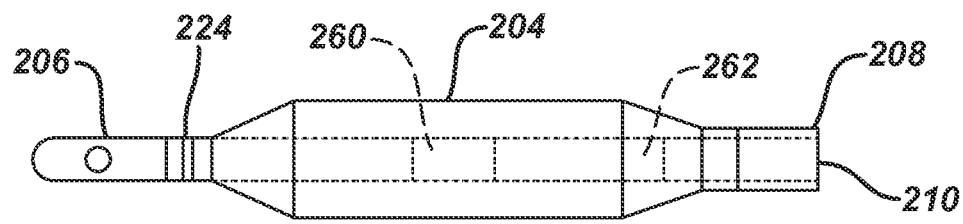
FIG. 2A is an enlarged top view of the distal end of the medical device of FIG. 2.

Referring now to FIG. 2, in a second embodiment, medical device 200 is an airway dilation and ventilating catheter and may include an integrated shaft system 202, a balloon 204 and a ventilating tip 206. The integrated shaft system 202 includes a distal shaft portion 216 and a proximal shaft portion 218 and the medical device has a distal end 220 and a proximal end 222. The distal shaft portion 216 is surrounded by a high pressure balloon 204 located near the ventilating tip 206. The ventilating tip 206 is soft and atraumatic for easy navigation to the site of the airway stenosis and protection of the airway from damage during insertion of the catheter. The shaft system 202 contains adjacent dual lumen tubing as described earlier with regard to FIG. 1A. Referring now to FIG. 2A as well as to FIG. 2, the inflation lumen 208 is used for inflation of the balloon with water, contrast medium or saline through inflation port 250 located near the proximal end 222 of medical device 200, and the ventilating lumen 210 permits passage of oxygen or air from the ventilation port 252 located near the proximal end 222 of medical device 200 to facilitate ventilation of the patient and prevent negative pressure pulmonary edema due to attempted breathing during the dilation procedure and the resultant airway blockage. The medical device 200 has a ventilating tip 206 with a slanted distal end 220 (in this case a 45 degree slant, but may be slanted between about 15 and 75 degrees and often between about 25 and 65 degrees), a forward facing tip opening 214 (with a diameter of between about 2 mm and 5 mm, often between about 3 mm, and 4 mm and in this case about 4 mm) and a radially facing opening 212 with a diameter of between about 2 mm and 6 mm, often between about 3 mm, and 5 mm and in this case about 4 mm) to facilitate air or oxygen flow through the ventilating lumen 210 for delivery before, during, or after dilation of the airway stenosis. The ventilating tip 206 is located on the distal shaft section 216, distal to the distal end of the balloon 204.

Figure 2B:
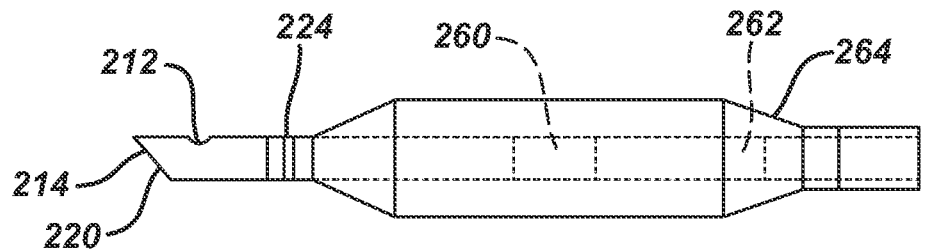
FIG. 2B is an enlarged side view of the distal end of the medical device of FIG. 2.

In the embodiment shown in FIGS. 2, 2A and 2B, direct visualization markers and/or radiographic markers may be disposed along the integrated shaft system 202 and in this case are disposed on the portion of the shaft that is surrounded by the balloon. The first shaft marker 260 is located at the mid-point of the balloon and may be positioned at the stenosis. The second shaft marker 262 is located in the proximal taper 264 of the balloon 202 and may be located proximally of the stenosis prior to inflation of the balloon and dilation of the stenosis. Any number of shaft markers may be located along the integrated shaft system inside or outside of the balloon and may be of the same or different lengths, and may be a single integral marker or may be single and double or even triple markers with the same or different colors to differentiate one from the other. In addition, the balloon may be marked or colored in order to more clearly visualize the position of the balloon in the patient's airway.

Figure 2C:
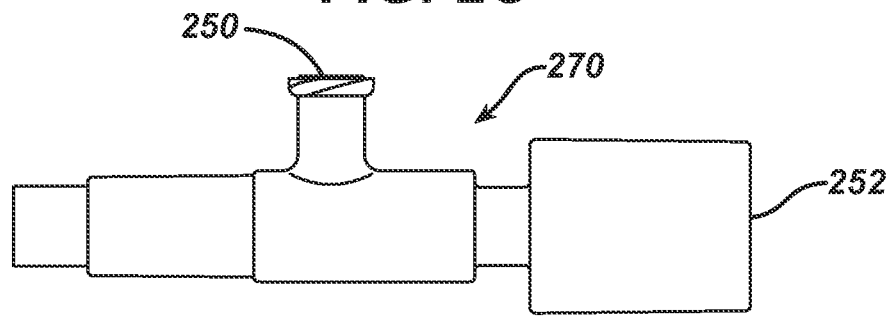
FIG. 2C is an enlarged side view of the connector of the medical device of FIG. 2.

The connector 270 of the device of FIG. 2 is shown in an enlarged view in FIG. 2C. The connector 270 has an inflation port 250 and a ventilation port 252. In order to ensure that the inflation medium (water, contrast medium or saline) is connected to the inflation port 250 and the ventilation port 252 is connected to the ventilation source (oxygen or air), the inflation port 250 and the ventilation port 252 are of different size, shape or type of connection. For example the inflation port 250 may be a threaded connector and the ventilation port 252 may be a non-threaded connector, or vise versa. One of the connectors may be a right-handed threaded connector, and the other may be a left-handed threaded connector. As shown in FIG. 2C, the inflation port 250 is much smaller in diameter (approximately 6 mm outer diameter) than the ventilation port 252 (approximately 20 mm outer diameter) and therefore could not be connected incorrectly. The difference in size of the different ports is that one port is at least about 10% larger than the other port, often at least about 50% larger and often about 100% larger than the other port.

The invention has been described with reference to certain examples or embodiments of the invention, but various additions, deletions, alterations and modifications may be made to those examples and embodiments without departing from the intended spirit and scope of the invention. For example, any element or attribute of one embodiment or example may be incorporated into or used with another embodiment or example, unless otherwise specified or if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. A medical device for dilating an airway stenosis, said device comprising:
    a proximal end;
    a distal end;
    a shaft system having an inflation lumen and a ventilating lumen between said proximal end and said distal end, the inflation lumen and the ventilating lumen being adjacent lumens, and said shaft system having a proximal shaft section and a distal shaft section;
    an inflatable balloon having an inflation diameter of between 5 mm and 14 mm and an inflation length of between 24 mm and 40 mm on said distal shaft section, proximal to the distal end of the medical device;
    a ventilating tip on the distal shaft section, distal to the inflatable balloon, said ventilating tip comprising a tip opening and one or more radially facing openings; and
    a connector on the proximal shaft section, said connector comprising a ventilation port and an inflation port,
    wherein the inflation lumen extends from the inflation port to the shaft system distal shaft section.

2. The medical device of claim 1 wherein the one or more radially facing openings comprise 4 openings.

3. The medical device of claim 2 wherein the radially facing openings have a diameter of between 1 mm and 2 mm.

4. The medical device of claim 2 wherein the radially facing opening are spaced 90 degrees apart.

5. The medical device of claim 1 further comprising an atraumatic tip portion.

6. The medical device of claim 1 further comprising one or more direct visualization markers.

7. The medical device of claim 6 wherein the markers are located on the shaft system.

8. The medical device of claim 6 wherein the markers are located on the balloon.

9. The medical device of claim 1 further comprising one or more radiographic markers.

10. The medical device of claim 1 wherein the ventilating tip comprises a soft and atraumatic tip portion.

11. The medical device of claim 10 wherein the soft and atraumatic tip portion is a slanted soft and atraumatic tip portion.

* * * * *